United States Patent [19]

Baust et al.

[11] Patent Number: 5,227,094
[45] Date of Patent: Jul. 13, 1993

[54] SHOWER GEL COMPRISING AN AMIDOPROPYBETAINE AND A FATTY ACID METHYLTAURIDE

[75] Inventors: Heinrich Baust, Plankstadt; Wolfgang Gross, Mutterstadt, both of Fed. Rep. of Germany

[73] Assignee: Joh. A. Benckiser GmbH, Ludwigshafen, Fed. Rep. of Germany

[21] Appl. No.: 571,145

[22] Filed: Aug. 23, 1990

[30] Foreign Application Priority Data

Aug. 31, 1989 [DE] Fed. Rep. of Germany ....... 3928773

[51] Int. Cl.$^5$ .............. C11D 1/28; C11D 1/88; C11D 1/94
[52] U.S. Cl. ................... 252/545; 252/546; 252/547; 252/DIG. 5
[58] Field of Search ........... 252/547, 545, DIG. 5, 252/546

[56] References Cited

U.S. PATENT DOCUMENTS

| 3,950,417 | 4/1976 | Verdicchio et al. | 252/545 |
| 4,110,263 | 8/1978 | Lindemann et al. | 252/545 |
| 4,181,634 | 1/1980 | Kennedy et al. | 252/545 |
| 4,375,421 | 3/1983 | Rubin et al. | 252/110 |
| 4,497,825 | 2/1985 | Bade | 514/556 |
| 4,861,517 | 8/1989 | Bade | 252/546 |
| 4,948,576 | 8/1990 | Verdicchio et al. | 424/59 |

FOREIGN PATENT DOCUMENTS

| 1283892 | 8/1972 | European Pat. Off. . |
| 127580 | 12/1984 | European Pat. Off. . |
| 194097 | 9/1986 | European Pat. Off. . |
| 2013235 | 8/1979 | United Kingdom . |

*Primary Examiner*—Paul Lieberman
*Assistant Examiner*—Erin M. Higgins
*Attorney, Agent, or Firm*—Foley & Lardner

[57] ABSTRACT

The present invention provides a shower gel having a tenside and other conventional adjuvants, for example thickening agents, electrolyte salts, perfume, coloring materials, disinfection agents and protein hydrolysates, as well as water as a solvent, wherein, as the tenside, there is used a combination of an amidopropylbetaine and a fatty acid methyltauride.

5 Claims, No Drawings

SHOWER GEL COMPRISING AN AMIDOPROPYBETAINE AND A FATTY ACID METHYLTAURIDE

BACKGROUND OF THE INVENTION

The present invention relates to a shower gel which reduces skin roughness.

Shower gels are commercially available and described in many publications with a great variety of compositions. The current trend is to shower more frequently, due to which skin irritations, which can progress as far as allergies, have recently occurred more frequently because of components included in the shower gels. Irritations of this kind are, in the first place, brought about by the tensides themselves included in the shower gels and, in particular, the alkyl sulphates and alkyl polyoxyethylene sulphates, which are used especially frequently because of their good foam formation, have proven to be strong skin irritants.

Recently, fears have also arisen that tensides which include polyoxyethylene structures are contaminated from their production by traces of dioxan or ethylene oxide and these can, in turn, have a skin-irritating effect.

SUMMARY OF THE INVENTION

It is therefore an object of the present invention to provide a new shower gel which is extremely skin compatible, contains no pharmacologically hazardous components but, with regard to the foam formation (height of foam, amount of foam and foaming-up behavior), as well as viscosity and temperature stability, is at least comparable with known shower gels.

In accomplishing the foregoing object there is provided according to the present invention a shower gel comprising, as a tenside, a combination of an amidopropylbetaine and a fatty acid methyltauride. Other known components for use in shower gels, for example, thickening agents, electrolyte salts, perfume, coloring material, disinfection agents, protein hydrolysates, refattening agents and the like, also can be included.

Further objects, features and advantages of the present invention will become apparent from the detailed description of preferred embodiments that follows.

DETAILED DESCRIPTION OF THE PREFERRED EMBODIMENTS

Both amidopropylbetaine and fatty acid methyltauride are known for their separate use as individual tensides in bath preparations, shampoos, foam baths and shower baths. Surprisingly, we have now found that a combination of these two groups of compounds in shower gels not only gives compositions which display an outstanding foam formation and stability and, therefore, as washing agents are comparable with or superior to the previously known shower gels, but that these agents also are extremely gentle on the skin and not only do not give rise to any skin irritation but instead reduce the skin roughness in comparison with a treatment with pure water and with solutions of the two components alone.

The shower gels according to the present invention preferably have the following composition: a shower gel including:
 about 5–15% amidopropylbetaine;
 about 2–10% fatty acid methyltauride;
 about 0–2% refattening agent;
 about 0–2% protein hydrolysate;
 about 0–2% perfume;
 about 0–1% coloring materials;
 about 0–5% electrolyte salts;
 about 0–2% thickening agent; and
 about 0–0.5% disinfection agent, with the remainder being water.

An amidopropylbetaine according to the present invention is understood to include compounds of the general formula:

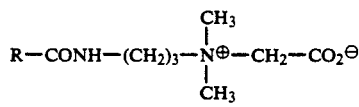

wherein R is a linear alkyl radical containing 7 to 17 carbon atoms.

A fatty acid methyltaurides in the meaning of the present invention are compounds of the general formula:

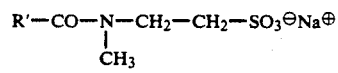

wherein R' is a residue of a fatty acid containing 8 to 20 carbon atoms which is saturated or unsaturated once or twice.

Apart from these tenside components, which enhance washing behavior and thickening and are added in a total amount of 7 to 25%, the shower gels according to the present invention can also include any conventional adjuvants for this purpose. Especially advantageous are refattening materials and protein hydrolysates which positively influence the structure of the skin, perfumes and coloring materials which increase the attractiveness of the product for the user, electrolyte salts and thickening agents which, together with the tensides, bring about the viscosity of the gel, and disinfection agents which, on the one hand, bring about the stability of the product during storage and, on the other hand, provide for an antibacterial action of the shower gel during use.

As a solvent preferably there is used dimineralized water, whereby pharmacologically compatible, water-soluble organic solvents, for example glycerol or the like, can also be present in small amounts.

The following Example is given for the purpose of illustrating the present invention:

EXAMPLE

Raw materials

| | |
|---|---|
| Tego betaine HS[1] | 9.42% |
| Hostapon CT[2] | 2.58% |
| collagen hydrolysate M[3] | 0.30% |
| Kathon CG | 0.08% |
| perfume oil | 1.0% |
| coloring material | q.s. |
| tap water | ad 100% |

Product data viscosity: about 5000 mPas
pH of concentrate: 6.9±0.1
1) = amidopropylbetaine
2) = fatty acid (C$_7$–C$_{17}$) methyltauride
3) = without M 100%

Experimental results

The testing of skin roughness took place on the inner side of the lower arm of 10 subjects with a 2% product solution in comparison with distilled water as reference.

Silicone impressions were first made not only of the test fields but also of the untreated remaining empty field. Microscope slides were thinly coated with a colorless silicone mass mixed with hardener and spread out with a coating bar to uniform thickness. The microscope slides were then placed with constant pressure on to the skin and removed after 2 minutes.

For testing purposes, the solution to be investigated is applied at an ambient temperature of C to the place to be treated, allowed to dry for minutes without mechanical action, carefully rinsed with water and dried. Thereafter, silicone impressions were again prepared.

After hardening for 24 hours, all the impressions were evaluated with the surface measurement apparatus Perthometer PRK. Average values of the depth of roughness $R_z$ according to German Industrial Standard DIN 4768 are given in μm in the following Table:

TABLE

| | Average values in μm. | |
|---|---|---|
| | blank field | preparation 1550 according to the present invention |
| blank value | 37.1 | 36.2 |
| after use for 10 minutes | 37.8 | 33.2 |
| differences | +0.7 | −3.0 |

We claim:

1. A shower gel without polyoxyethylene-containing compounds consisting essentially of:

from 2 to 10% by weight of the composition of a fatty acid methyltauride represented by the formula B:

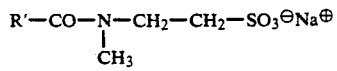

wherein R' is a fatty acid residue having 8 to 20 carbon atoms; and from 5 to 15% by weight of the composition of an amidopropylbetaine represented by formula A:

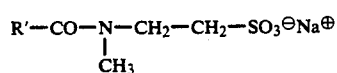

wherein R is a linear alkyl radical having 7 to 17 carbon atoms.

2. A shower gel as recited in claim 9, comprising:
about 5-15% amidopropylbetaine;
about 2-10% fatty acid methyltauride;
about 0-2% refattening agent;
about 0-2% protein hydrolysate;
about 0-2% perfume;
about 0-1% coloring material;
about 0-5% electrolyte salt;
about 0-2% thickening agent; and
about 0-0.5% disinfection agent, wherein the remainder comprises water.

3. A shower gel as recited in claim 1, wherein R' is a saturated fatty acid residue.

4. A shower gel as recited in claim 1, wherein R' is a fatty acid residue having at least one unsaturated bond.

5. A shower gel as recited in claim 1, wherein R' is a fatty acid residue having two unsaturated bonds.

* * * * *